(12) United States Patent
Soffer (10) Patent No.: US 11,826,233 B2
(45) Date of Patent: Nov. 28, 2023

(54) DEVICE TO BE DEPLOYED AND RETAINED IN TWO OPPOSITE CAVITIES

(71) Applicant: Guy Soffer, Kiryat Ono (IL)

(72) Inventor: Guy Soffer, Kiryat Ono (IL)

( * ) Notice: Subject to any disclaimer, the term of this patent is extended or adjusted under 35 U.S.C. 154(b) by 226 days.

(21) Appl. No.: 15/733,338

(22) PCT Filed: Jan. 2, 2019

(86) PCT No.: PCT/IL2019/050004
§ 371 (c)(1),
(2) Date: Jul. 1, 2020

(87) PCT Pub. No.: WO2019/135220
PCT Pub. Date: Jul. 11, 2019

(65) Prior Publication Data
US 2021/0113382 A1    Apr. 22, 2021

(30) Foreign Application Priority Data

Jan. 2, 2018   (IL) .......................................... 256701

(51) Int. Cl.
*A61F 11/00* (2022.01)
*A61M 31/00* (2006.01)
*A61F 11/20* (2022.01)

(52) U.S. Cl.
CPC .......... *A61F 11/202* (2022.01); *A61M 31/00* (2013.01); *A61M 2205/0216* (2013.01); *A61M 2205/0288* (2013.01); *A61M 2205/0294* (2013.01); *A61M 2205/584* (2013.01); *A61M 2205/587* (2013.01); *A61M 2210/0675* (2013.01); *A61M 2210/1425* (2013.01)

(58) Field of Classification Search
CPC ................. A61F 11/202; A61M 31/00; A61M 2205/0216; A61M 2205/0288;
(Continued)

(56) References Cited

U.S. PATENT DOCUMENTS 5,061,255 A * 10/1991 Greenfeld ......... A61M 25/0029
604/35
6,599,297 B1 * 7/2003 Carlsson ............... A61F 11/202
604/174

(Continued)

FOREIGN PATENT DOCUMENTS

DE    10 2009 042249 A1    5/2011
DE    10 2012 218164 A1    6/2014
(Continued)

*Primary Examiner* — Adam Marcetich
*Assistant Examiner* — Rachel O'Connell
(74) *Attorney, Agent, or Firm* — Vorys, Sater, Seymour and Pease LLP; Anthony P. Venturino; Maryellen Feehery Hank (57) ABSTRACT

Provided is a medical device with portions configured for fitting and being retained simultaneously into two cavities on opposite sides of the body of a subject, for example the eustachian tubes or the fallopian tubes. The device may include an elongated member with a central segment and first and second peripheral segments extending therefrom. These segments differ in their intended function and eventual in situ positioning: the two peripheral segments intended for insertion and positioning within the two cavities and exerting their function within the cavities. The central segment serves as a link between two peripheral segments and may also be used for some other functions by its position. The elongated member may have elastic properties.

22 Claims, 10 Drawing Sheets

(58) Field of Classification Search
CPC .... A61M 2205/0294; A61M 2205/584; A61M 2205/587; A61M 2210/0675; A61M 2210/1425
See application file for complete search history.

(56) References Cited

U.S. PATENT DOCUMENTS

| | | | |
|---|---|---|---|
| 2005/0000520 A1* | 1/2005 | Silman | A61F 11/202 128/207.18 |
| 2007/0233036 A1* | 10/2007 | Mandpe | A61F 11/202 604/93.01 |
| 2013/0253387 A1 | 9/2013 | Bonutti et al. | |
| 2015/0075536 A1* | 3/2015 | Brenzel | A61F 6/225 128/831 |
| 2015/0202089 A1* | 7/2015 | Campbell | A61B 5/6852 600/478 |
| 2015/0305943 A1* | 10/2015 | Hossainy | A61M 29/02 604/514 |
| 2017/0252089 A1* | 9/2017 | Hester | A61B 18/1485 |

FOREIGN PATENT DOCUMENTS

| | | |
|---|---|---|
| WO | 2007/100790 A2 | 9/2007 |
| WO | 2007/111636 A2 | 10/2007 |
| WO | 2008/045242 A2 | 4/2008 |
| WO | 2009/001358 A2 | 12/2008 |
| WO | 2009/091560 A1 | 7/2009 |

* cited by examiner

DEVICE TO BE DEPLOYED AND RETAINED IN TWO OPPOSITE CAVITIES

TECHNOLOGICAL FIELD

The present disclosure relates to a medical device, more specifically a device deployable in an anatomical cavity.

BACKGROUND ART

References considered to be relevant as background to the presently disclosed subject matter are listed below:
WO 2007/100790
WO 2007/111636
WO 2008/045242
WO 2009/001358

Acknowledgement of the above references herein is not to be inferred as meaning that these are in any way relevant to the patentability of the presently disclosed subject matter.

BACKGROUND

Otitis media is a group of inflammatory diseases of the middle ear and one of the most common diagnosed sickness in children. One of the main causes of Otitis media is a dysfunction of the Eustachian tube, namely a blockage or stenosis thereof. The Eustachian tube links the nasopharynx to the middle ear and is part of the latter. The Eustachian tube is the only link of the middle ear to the outside atmosphere. Typically, the Eustachian tube is in a collapsed state, not permitting air flow between the middle ear and the nasopharynx but upon the need of equilibration of pressure, for example when there is an ambient pressure change, the Eustachian tube is openable by swallowing or by induced positive pressure from the middle ear towards the nasopharynx. A case of a blockage in the Eustachian tube may lead to an Eustachian tube disorder (ETD) that may involve accumulation of fluids (that may become infected) in the middle ear, speech and balance problems or changes in the structure of the ear drum. In order to prevent ETD or Otitis media many solutions are available, such as piercing the ear drum and implanting a pressure equalization tube therein to maintain equilibration between the ambient pressure and the middle ear. WO 2007/100790 and WO 2009/001358 suggest inserting a device into the Eustachian tube as a treatment or prevention of ETD. More solutions are suggested in WO 2007/111636 and WO 2008/045242.

General Description

The present disclosure provides a medical device with portions that are configured for fitting and being retained simultaneously into two cavities on opposite sides of the body of a subject, and in some specific embodiments two sides of the skull. When referring to two sides of the body, it means the two sides with respect to a symmetrical axis of the body. For example, at one side of the body there is one eye and the second is located on the other side, one nostril is at one side and the other is in the other sides, etc. The subject may be a human subject or a non-human animal. The device may comprise an elongated member with a central segment and first and second peripheral segments extending therefrom. These segments differ in their intended function and eventual in situ positioning: the two peripheral segments intended for insertion and positioning within the two cavities and exerting their function within the cavities. The central segment serves as a link between two peripheral segments and may also be used for some other functions by its position. The elongated member may have elastic properties.

By one embodiment of the present disclosure, these three segments are continuous and not discernible from one another. For example, all three segments may have the same overall configuration with no discernible borders or demarcations between them, the division into segments being only functional in accordance with their intended deployed position.

By another embodiment, the segments are clearly defined, for example by a different appearance and configuration (e.g. the peripheral segment comprising a helical or stent-like portion) or, for example, may be separated by a functional element, such as an elastic portion.

In some embodiments of the device, the elongated member is configured to be in physical contact with or in proximity to the soft-pallet, such that movements of the soft-pallet are inducing vibrations or movements of the device.

The device is configured to be deployed such that its peripheral segments fit into first and second cavities on opposite sides of a skull of a subject. By some embodiments, the two peripheral segments are, typically, but not exclusively, symmetrical with respect to a midline at said central segment.

The peripheral segments are adapted for inserting into and to be retained within the cavities. The device has typically at least two configurations—a deployment configuration, assumed prior and during deployment and a deployed configuration in which it is deployed and retained within the cavities. In the deployed configuration, the two peripheral segments are positioned within the opposite cavities of the skull and being integrally linked by the central segment.

While in a deployed configuration, chewing or swallowing by the subject can cause a movement or vibration of the central segment and hence of the entire device and by that, where the cavities are the Eustachian tubes, ventilate the middle ear.

The device can be configured for deployment in variety of cavities of the skull such as Eustachian tubes, sinuses, nasal cavities. In a more general sense, the device can be deployed in a variety of body cavities. One example is inside the womb while connecting the two fallopian tubes. A device configured for deployment in the Eustachian tubes is a particular embodiment of this disclosure.

In some embodiments, the device comprises one or more sections made of an elastic or flexible element such as a spring, e.g. in the form of a helical coil. In some other embodiments, the at least one peripheral segment is configured as or comprises a stent element.

In some embodiments, the peripheral segment comprises an expansion member configured to expand the cavity while applying pressure onto the cavity walls. The expansion member can be in a form of inflatable/collapsible element such as balloon or in a form of expandable/foldable elements such as wings. The expansion members are actuated through an actuator and can be switched from one state to another.

In some embodiments, the elongated member is tubular with at least one central port, e.g. at the central segment, and at least two peripheral ports at the peripheral segments. This arrangement permits the delivery of a therapeutic substance introduced through the central port into the cavities, drainage or pumping of liquids or gas into or away from the cavities (e.g. equalizing pressure or pumping gas which may be air, oxygen, nitrogen, carbon dioxide, etc., into the cavity to thereby clearing a blockage).

The device has, typically, a deployment state in which it is brought initially into position and a deployed state assumed by it after its deployment in situ. By one embodiment the device is configured to be biased into a deployed state, such that during deployment it is restrained in the deployment state and then released once in position to thereby switch into the deployed state. By another embodiment, the switching of the device from a deployment state into a deployed state is by forced manipulation.

The device, and specifically the elongated member, may be made of biocompatible materials, may be made of metal (e.g. nitinol), plastic material, silicon, etc., or any combination thereof.

In some embodiments, the device includes at least one vibrations-inducing element, typically associated with the central segment, configured for inducing vibrations onto the elongated member. Vibrations of the elongated member can induce a dilation of the cavity or opening of a blocked or clogged passageway and consequently an expulsion of blocking fluids or solids. In some embodiments, the vibrating element comprises a magnet or an electric coil that can be induced to vibrate by an external magnetic field or a piezoelectric member that can be induced to vibrate by an external electric field. In some other embodiments the vibrations-inducing element is at least one piezoelectric element, typically associated with the central segment. In some other embodiments, the piezoelectric element is embedded in the elongated member.

The device can have at least one sensor for sensing one or more physiological or device-associated parameters. The sensed data can be recorded in a local memory or be transmitted periodically or in real-time (by wireless communication) to an external device using RF, Bluetooth, other low-energy transmitters, etc.

In some embodiments of the device, the peripheral segments have at least one head unit. The head unit structure can be altered between a deployment and deployed states and can be utilized for anchoring the device in the cavity. Furthermore, the head unit can serve the function of a unidirectional valve intended to permit flow of fluids in the cavity generally in one direction. It is to be noted that in some embodiments the elongated member is configured with or comprises stopper elements for preventing the device from sliding too deeply into the cavity.

In a specific embodiment of the device, the head unit has a screw like shape and is configured to spin along its longitudinal axis to thereby advance into the cavity in a screw-like manner while at the same time pushing or forcing fluids backwards towards the nasal cavity.

In some embodiments, the device has at least one weight fixed to or integral with the elongated member. The weight is typically positioned at and associated with the central segment, e.g. about a midline, and is intended to amplify the vibrations and add momentum to the vibrating elongated member.

The device can have radio frequency (RF) transducers, typically proximal to one of the ends, to aid tissue recovery.

In some embodiments of the device, the elongated member may include markings that are indicative of the length of the elongated member. Namely, by observing a marking, a user of the device can learn about the distance from one end or from a mid-portion to the point of the marking. Thus, when the device is deployed, the marking may indicate the depth of the Eustachian tube.

In some embodiments of the system, the markings are indicative of the length from a mid-portion of the elongated member towards one or both distal ends thereof. In some embodiments of the system, different lengths are discernable by different colors of the markings. Namely each marking identifies the length of the portion of the elongated member, from its location towards an end or towards a mid-portion of the elongated member, by its color.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The disclosed subject matter will be described in connection with FIGS. 1-10 exemplifying the presently disclosed subject matter in connection with Eustachian tubes for the relief of Otitis media.

Figure 1A:
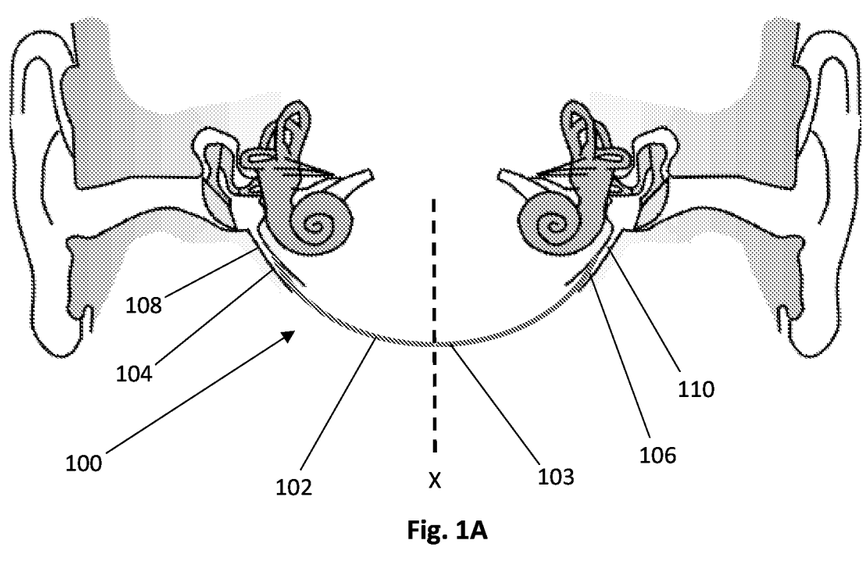
FIGS. 1A-1C, FIG. 2, FIG. 5 and FIG. 6 are schematic illustrations of devices according to embodiments of this disclosure with their two peripheral segments positioned within the Eustachian tubes.

FIG. 1A shows device 100 configured as a continuous elongated member 102 with a central segment 103 and two peripheral segments 104, 106 extending therefrom. Device 100 is symmetrical with respect to midline of the body (X axis) and is shown herein in its deployed state with its two peripheral segments 104, 106 positioned within a subject's Eustachian tubes 110 and 108, respectively.

Figure 1B:
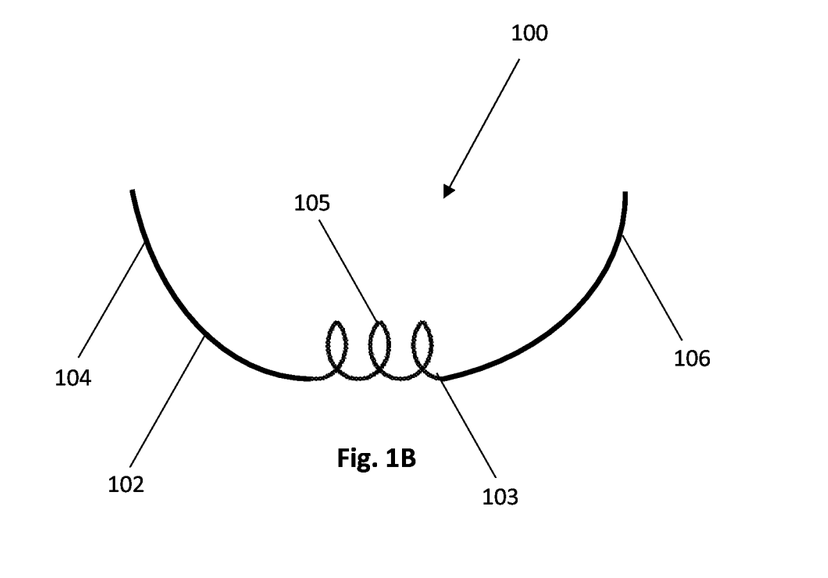
Figure 1C:
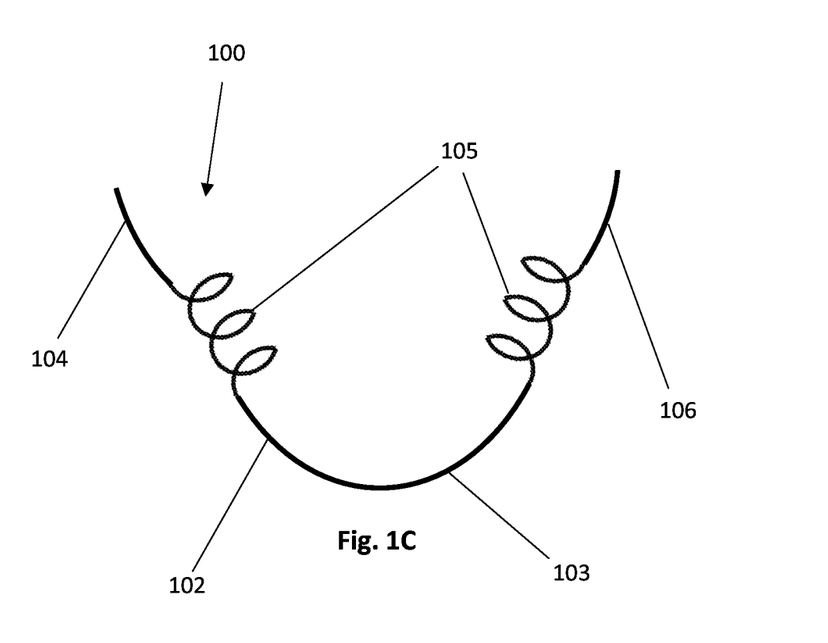

As schematically illustrated, elongated member 102 is substantially uniform throughout its length. However, alternative embodiments, where this is not the case, will be exemplified in the description below. By way of example, the elongated member may have integral elasticity-inducing elements, such as element 105 in FIGS. 1B and 1C, such as a spring, e.g. helical coil, integrally formed within the elongated member. The elastic element may, for example, be a single element formed within the central segment or such elements formed between the central segment and the peripheral segments. Such configurations are schematically shown in FIGS. 1B and 1C, respectively.

Figure 8A:
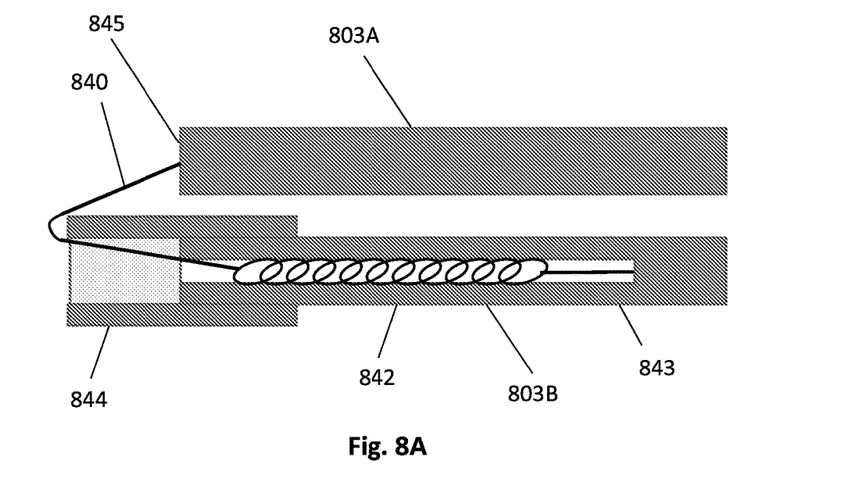
FIGS. 8A-8B are schematic illustrations of a deployment configuration and a deployed configuration of a device according to another embodiment of the present disclosure.
Figure 8B:
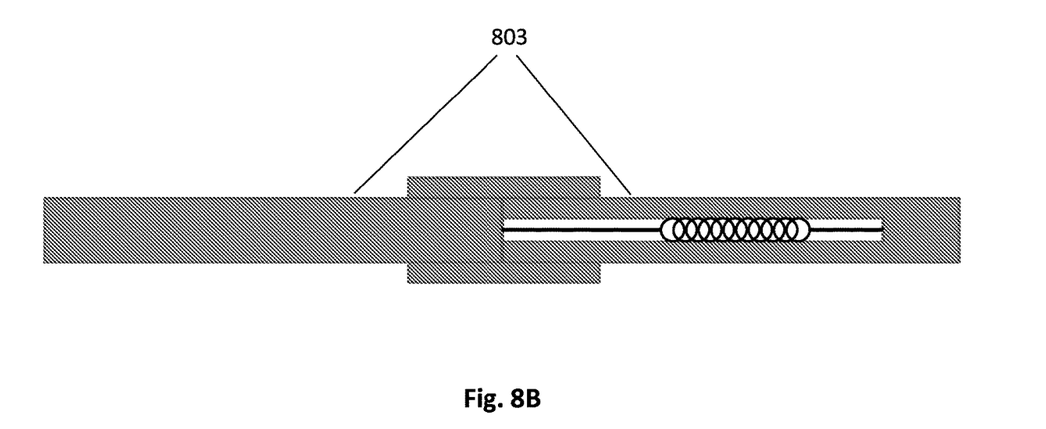

The device typically has a deployment state and a deployed state. The device is typically brought into position by a suitably configured applicator (not shown), in a deployment state in which it may be bent, e.g. about a midline, brought into position and then switched into a deployed state with its two end segments deployed in cavities formed at opposite sides of the skull. Such an applicator typically has two guiding ends, each is configured to guide the delivery of the device into a different side of the skull's cavities. The guiding ends accommodate an image acquisition device, e.g. a camera, transmitting the acquired video or image data, through wireless communication, to a receiving system, namely a monitor, that is capable of presenting a real-time video or images received from the camera. The guiding ends also accommodate a light source for lighting at least a portion of the field of view of the camera. Switching between the deployment state and the deployed state may be through an intrinsic bias of the elongated member, in which case the device will be constrained by the applicator in the deployment state, switching spontaneously into the deployed state once the constraint is released. Alternatively, such switching between the two states may be through a forced manipulation. Switching between the deployment state and the deployed state can be achieved, by one embodiment through plastic deformation of the segments of the device. A switching mechanism according to one exemplary embodiment is illustrated schematically in FIGS. 8A-8B. FIG. 8A shows a deployment configuration of a device 800 having a central segment 803 that is divided into two individual sub-segments 803A and 803B which are connected by a wire 840 that is attached or linked to a spring 842, contained within a lumen 843 formed within sub-segment 803B. In this state, spring 842 is in a stretched state. Each of sub-segments 803A, 803B can be deployed into a respective cavity and after being in position, the biasing action of the spring 842 causes the proximal portion 845 of sub-segment 803A to snap into position with the coupling receptacle 844 as seen in FIG. 8B.

Once the device is in position and secured within both cavities, by actuating a releasing mechanism in the applicator, the applicator is released from the device. The device may then be left in the cavities for a certain amount of time, according to a decision of a practitioner. Once the treatment is over the device is removed by a removal applicator. The removal applicator has two grabbing arms that are configured to be inserted through the nostrils and grab at least a portion of each side of the device for safe removal thereof. Before the removal of the device, it can be cut into two sections such that each section is being held by one grabbing arm.

The device, by some embodiments, may have functional peripheral elements.

In FIGS. 2, 3, 4, 5 and 6, like elements to those of FIG. 1 were given like reference numerals shifted, respectively, by 100, 200, 300, 400 and 500. Thus, for example, element 202 in FIG. 2, serves the same function as element 102 in FIG. 1.

Figure 2:
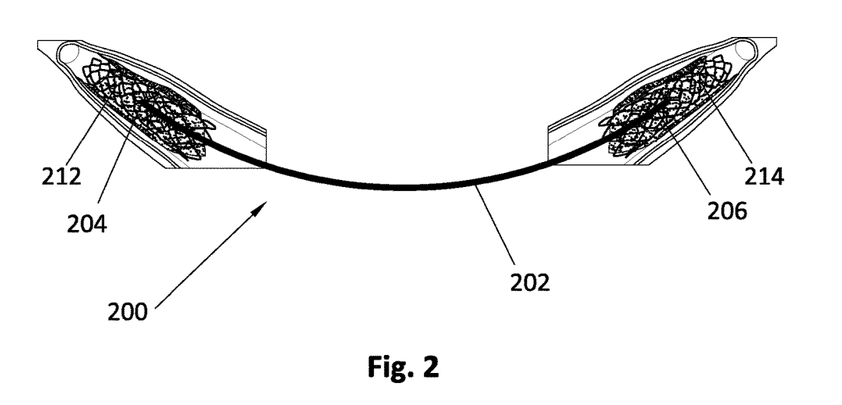

Reference is now being made to FIG. 2 showing a schematic illustration of another exemplary, non-limiting embodiment of this disclosure, in which the peripheral segments comprise stent elements 212, 214. The stent has a deployment state where it has a narrow cross-section and then, once in situ, it is extended to assume the deployed state, shown in FIG. 2. In another embodiment the stent elements are fixed or loosely coupled to the peripheral segments via a connecting member (e.g. a wire, suture, etc.) to limit the axial movement along the tube and thereby reduce risk that the stents, coupled to the device, will slide into the nasopharynx.

Figure 3:
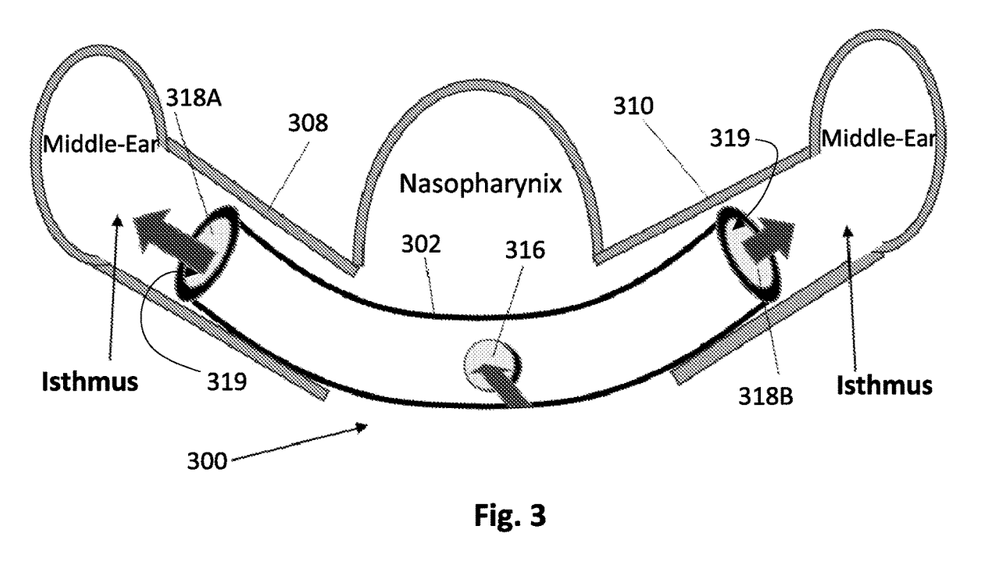
FIG. 3 is a schematic illustration of a device according to another embodiment of this disclosure that has an overall tubular structure.

Another configuration of the device of this disclosure is exemplified in the schematic (and entirely not to scale) illustration of FIG. 3. The elongated member of this embodiment has a general tubular structure with a lumen 319 and central entry port 316 and two peripheral ports 318A, 318B. The central port may by one embodiment serve for the introduction of a medicament to be delivered into the middle ear through ports 318A, 318B. Alternatively, the device of such a configuration may serve to drain excess fluid from the middle ear, passing through ports 318A, 318B, through lumen 319 and then out of port 316.

Figure 4:
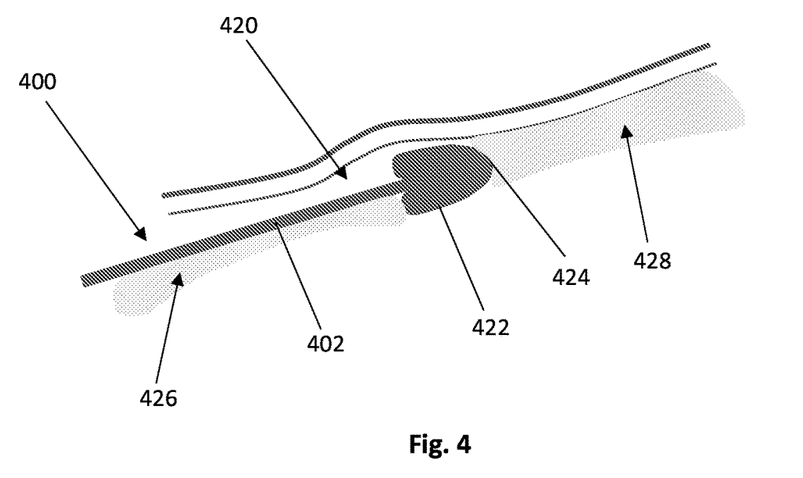
FIG. 4 is a schematic illustration of a peripheral segment of a device according to another embodiment of this disclosure within an Eustachian tube that has a head unit that functions as a uni-directional valve intended to permit flow of fluids in the cavity generally in one direction.

FIG. 4 is a schematic view of a peripheral segment, according to another embodiment, deployed in cavity 428, for example, the Eustachian tube, where the end portion is configured as a unidirectional valve 422 permitting flow of fluid 426 along the cavity in only one direction. The unidirectional valve effect may be achieved either by the end portion alone or in a combination effect achieved by association of the end portion and the wall of the cavity and may depend on the viscosity of the fluid and on cavity wall flexibility.

Figure 5:
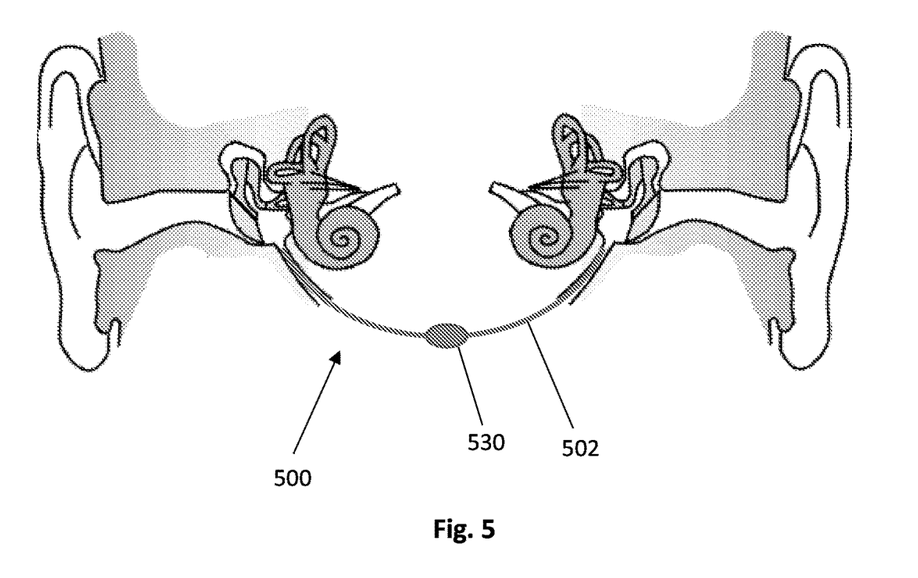

FIG. 5 shows an embodiment of a device of this disclosure that has a similar configuration to that shown in FIG. 1 with the difference being the inclusion of a weight 530 fixed at the central segment about the midline. This weight adds to augment the natural vibration, as explained above.

Figure 6:
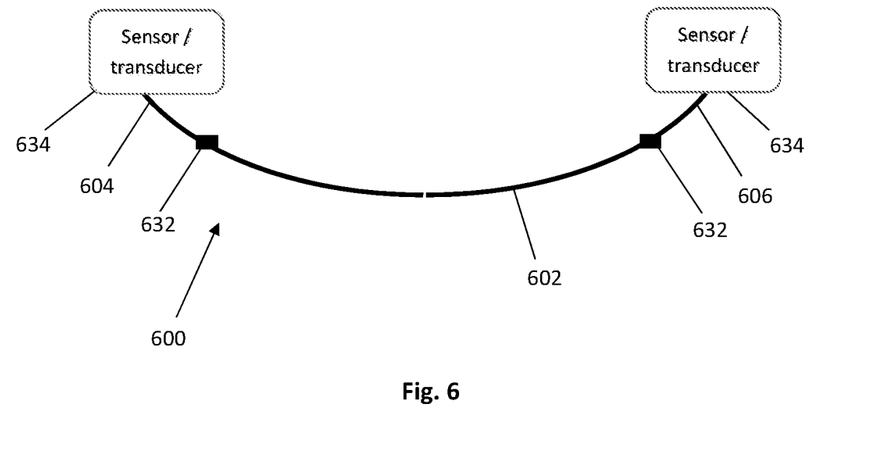

FIG. 6 shows a schematic illustration of another embodiment of a medical device 600, in which piezoelectric elements 632 are placed along the elongated member 602. The piezoelectric elements 632 may react to external electric potential (which may be imparted by a separate device outside the skull), its activation inducing bending or vibrations of member 602. The peripheral segments 604, 606 comprise sensors or transducers 634. The sensors and transducers can be for example: RF transducers to aid tissue recovery, sound speakers (e.g. piezoelectric) to re-generate sound waves to a patient whose middle-ear does not function well, camera for transmitting images or any other sensor for providing data related to the cavity or device state.

Figure 7A:
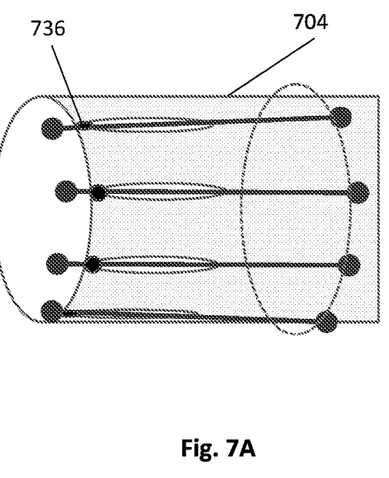
FIG. 7A-7B are schematic illustrations of a collapsible/expandable structure of the peripheral segment of a device according to another embodiment of this disclosure.
Figure 7B:
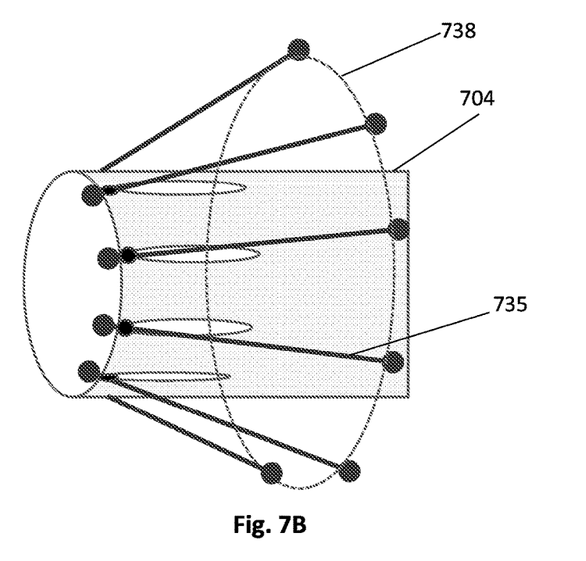

FIGS. 7A and 7B are schematic views of a peripheral segment 704 of a device, according to yet another embodiment, showing collapsible/expandable structure configuration. The peripheral segment 704 has a plurality of pins 735 that are articulated to the peripheral segment 704, e.g. by a hinge 736. Upon actuation by an actuator (not shown) the pins 735 pivotally displace in the general radial direction to their open, expanded position thus temporarily increasing the effective diameter of the peripheral segment 704, represented by circular dotted line 738. It is possible, in accordance with other embodiments, to overlay pins 735 with a flexible sheet such that once the rod are opened, they form, jointly with the sheet, a generally umbrella-like structure. The opening may be a one-time event or, alternatively, the array of pins may be switched continuously or intermittently between their collapsed and expanded states.

By yet other embodiments, the peripheral segment 704 may have two or more arrays of expandable pins, of the kind shown in FIGS. 7A-7B, scattered there along. The actuation of all such arrays may be all simultaneous or not; for example the different arrays may be actuated periodically to jointly define a propagating spatial wave which mimics peristaltic motion to assist fluid flow along the cavity. Peristaltic wave motion direction can be from nasopharynx to middle ear or in the opposite direction. Switching of the pins between their collapsed and expanded states may be done in a variety of mechanical means known per se.

Figure 9A:
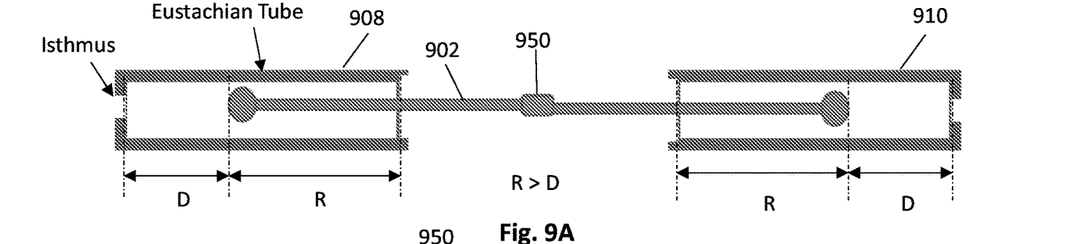
FIG. 9A-9B are schematic illustrations of a device of another embodiment deployed in the Eustachian tubes and confined therein.
Figure 9B:
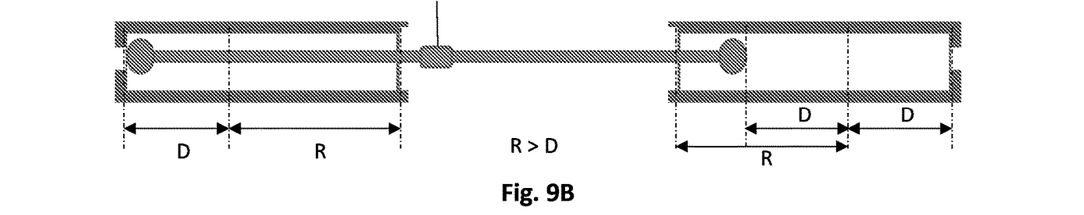

FIGS. 9A-9B illustrate an embodiment of the device of the present disclosure where the two peripheral segments are coupled to a connector 950 in a releasable manner. While deployed, the device is confined within the Eustachian Tubes as exemplified in FIGS. 9A-9B. In other words, even in the extreme case where the device is displaced to one side of the skull and its tip reaches the edge of the Eustachian Tube (namely, the Isthmus), as seen in FIG. 9B, it is still safely secured and confined within the two Eustachian Tubes without the risk of falling into the trachea or the lungs in any orientation of the body. For this, the dimensions of the device should be guided by those of the Eustachian Tube; namely, the length of the device is longer than the gap between the two Eustachian Tubes and should occupy at least half of the Eustachian Tube length on each side (R>D). The peripheral segments can be released from the connector 950, e.g. by an actuator, such that the device can be removed safely from the tubes.

Figure 10A:
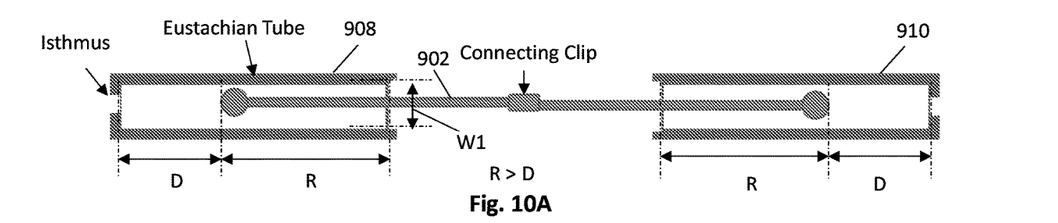
FIG. 10A-10D are schematic illustrations of a device of an embodiment of this disclosure deployed in Eustachian tubes and showing its lumen dilation effect while vibrating.
Figure 10B:
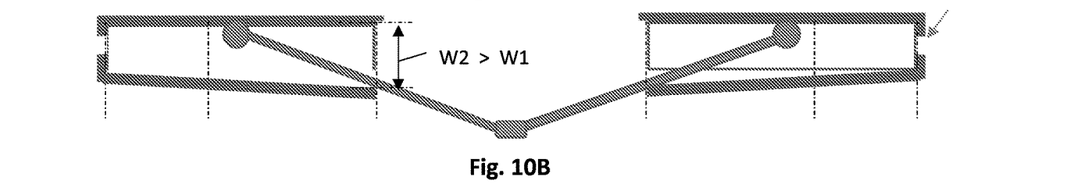
Figure 10C:
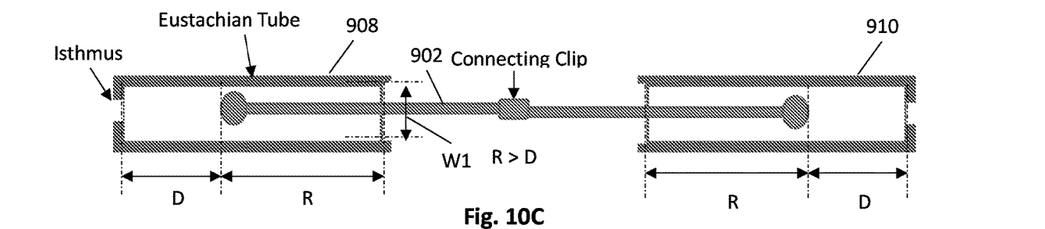
Figure 10D:
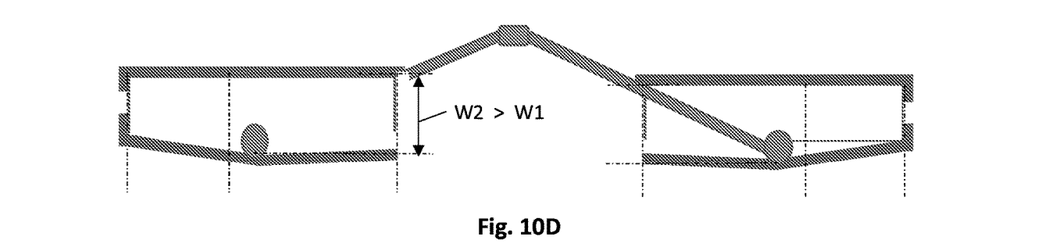

FIGS. 10A-10D show a device according to an embodiment of this disclosure that can be induced into oscillations (either by the subject's motion, by the flow of air while inhaling/exhaling, by an external induction, etc.). The oscillations cause a periodical dilation of the Eustachian Tubes, as exemplified in FIGS. 10A to 10D, whereby the opening of the tube increases from an initial width W1 (FIGS. 10A and 10C) to W2 (FIGS. 10B and 10D).

Other examples of body cavities for which device of different embodiments of this disclosure may be used include the uterus where the first end of the device may be inserted into one fallopian tube and the second end into the other fallopian tube on the other side. Such a device may comprise a tube with a proximal end in the vagina, permitting a medical practitioner to inject substances that should reach the fallopian tubes or the ovaries.

Figure 11:
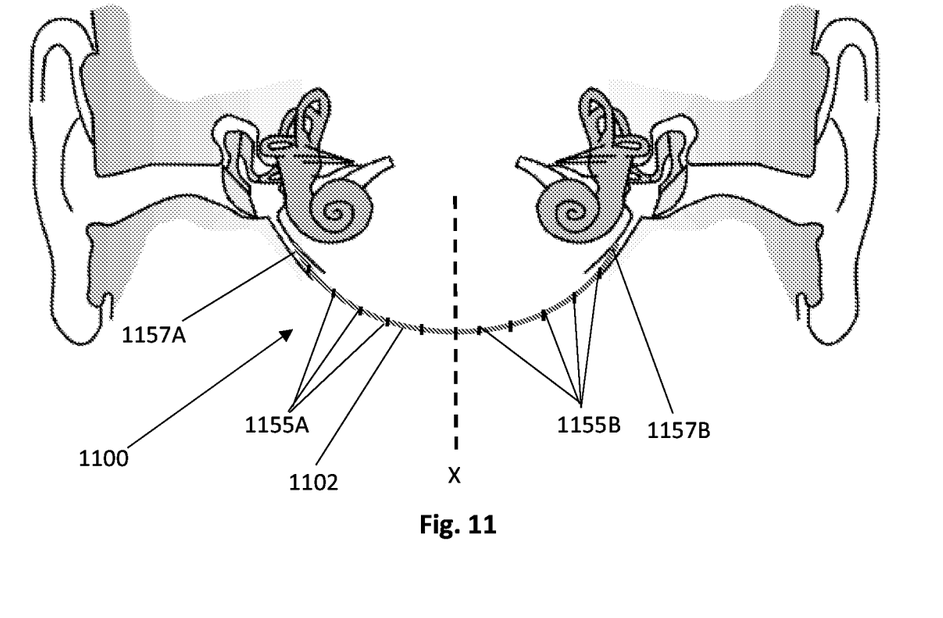
FIG. 11 is a schematic illustration of a non-limiting example of an embodiment of the device of the present disclosure.

Reference is now made to FIG. 11 which is a schematic illustration of a non-limiting example of an embodiment of the device of the present disclosure. The elongated member 1102 of the device 1100 includes markings 1155A and 1155B at the left and right side of the elongated member 1102, respectively. In this specific example, the markings 1155A, 1155B indicate the length from a mid-portion of the elongated member defined on axis X towards first and second ends 1157A, 1157B of the elongated member 1102, respectively. For example, each of the markings can carry a different color, indicating a different length along the elongated member 1102.

The invention claimed is:

1. A device for deployment within a body of an animal or a human subject, comprising
an elongated member comprising a central segment, first peripheral segment and second peripheral segment each extending from the central segment, the first peripheral segment adapted for deployment and retention in a first cavity at one side of the body, the second peripheral segment adapted for deployment and retention in a second cavity at an opposite side of the body, and the central segment adapted to be disposed at an area between the first and second cavities;
wherein after reaching a deployed state, the device in its entirety is free of attachment to the tissue such that the device can at least partially move or vibrate; in the first cavity and in the second cavity, and wherein a length of the device is longer than a gap between the first cavity and the second cavity.

2. The device of claim 1, wherein the device is symmetrically formed about a mid-portion.

3. The device of claim 1, wherein the first and second cavities are on two opposite sides of a skull in the body.

4. The device of claim 1, wherein the first and second cavities are Eustachian tubes, sinuses and nasal cavities.

5. The device of claim 1, wherein the elongated member is at least partially formed of one or more helical coils and springs.

6. The device of claim 1, wherein the elongated member is tubular.

7. The device of claim 6, wherein the elongated member comprises three ports configured for delivering therapeutic substances, introducing pressurized gas or drainage of fluids or solids.

8. The device of claim 1, wherein one of the peripheral segments of the elongated member comprises or in a physical connection with a stent.

9. The device of claim 1, wherein the device has a deployment state and a deployed state and is biased into the deployed state.

10. The device of claim 1, wherein the elongated member is made of biocompatible and elastic flexible materials.

11. The device of claim 1, further comprising one vibration inducing element configured for inducing vibrations of the elongated member.

12. The device of claim 11, wherein the one vibration inducing element comprises one of:
a magnetic member capable of inducing vibrations by an external magnetic field; and an electric coil member capable of inducing vibrations by an external magnetic field; and
a piezoelectric member capable of inducing vibrations by an electric field.

13. The device of claim 12, further comprising one sensor for sensing a cavity-related and a device-related parameter and a transmitter for transmitting the sensed parameter.

14. The device claim 1, wherein the first and second peripheral segments each comprises one head unit.

15. The device of claim 14, wherein the head unit is a unidirectional valve.

16. The device of claim 1, wherein tips of the first and the second peripheral segments are capable of movement at a confined extent with respect to a tissue when in deployed state.

17. The device of claim 1, comprising a weight fixed to or integral with the elongated member.

18. The device of claim 1, comprising a piezoelectric element configured for maneuvering the elongated member.

19. The device of claim 1, wherein the central segment, first peripheral segment and second peripheral segments are continuous and not discernible from one another.

20. The device of claim 1, wherein the elongated member comprises markings indicative of a length thereof.

21. The device of claim 1, wherein movement of the deployed device comprises one or both of: lateral movement in the direction of either the first and second cavities, and vertical movement with respect to a midline axis crossing the central segment.

22. The device of claim 1, wherein the area between the first and second cavities interconnects the first and second cavities.

* * * * *